Figure 1:
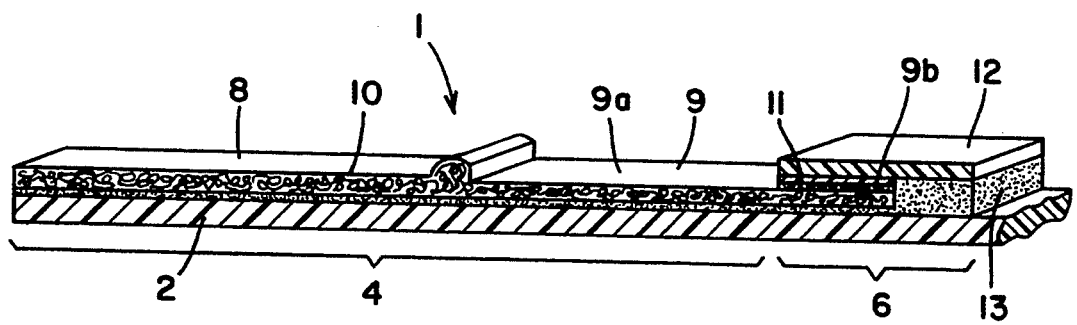

United States Patent [19]

Schlipfenbacher et al.

[11] Patent Number: 5,338,513
[45] Date of Patent: Aug. 16, 1994

[54] TEST CARRIER FOR THE ANALYTICAL DETERMINATION OF A COMPONENT OF A LIQUID SAMPLE

[75] Inventors: Reiner Schlipfenbacher, Lampertheim; Joachim Steinbiss, Lorsch; Heinz-Friedrich Trasch, Ludwigshafen, all of Fed. Rep. of Germany

[73] Assignee: Boehringer Mannheim GmbH, Mannheim, Fed. Rep. of Germany

[21] Appl. No.: 32,757

[22] Filed: Mar. 17, 1993

Related U.S. Application Data

[63] Continuation of Ser. No. 814,183, Dec. 19, 1991, abandoned, which is a continuation of Ser. No. 384,982, Jul. 25, 1989, abandoned.

[30] Foreign Application Priority Data

Jul. 30, 1988 [DE] Fed. Rep. of Germany ....... 3826056

[51] Int. Cl.$^5$ ............................................ G01N 31/22
[52] U.S. Cl. ........................................ 422/56; 422/57; 422/58; 435/805
[58] Field of Search ................................ 422/55–60; 435/805

[56] References Cited

U.S. PATENT DOCUMENTS

| 4,477,575 | 10/1984 | Vogel et al. | 422/56 X |
| 4,780,280 | 10/1988 | Berger et al. | 422/58 X |
| 4,780,411 | 10/1988 | Piejko et al. | 422/56 |
| 4,806,311 | 2/1989 | Greenquist | 422/58 X |
| 4,820,644 | 4/1989 | Schäfer et al. | 422/55 X |
| 4,839,297 | 6/1989 | Freitag et al. | |
| 4,861,711 | 8/1989 | Friesen et al. | |
| 4,891,313 | 1/1990 | Berger et al. | 435/7.94 |

FOREIGN PATENT DOCUMENTS

| 0274911 | 7/1988 | European Pat. Off. |
| 3643516 | 6/1988 | Fed. Rep. of Germany |
| 8604683 | 8/1986 | PCT Int'l Appl. |

*Primary Examiner*—James C. Housel
*Assistant Examiner*—Arlen Soderquist
*Attorney, Agent, or Firm*—Felfe & Lynch

[57] ABSTRACT

A test carrier for the analytical determination of a component of a liquid sample, especially for the diagnosis of diseases, in which a reaction sequence taking place on a test carrier having a base layer, a liquid transport path which extends from a sample application region to an evaluation region and a signal formation layer in which, on the basis of a signal formation reaction, with the help of a signal formation reagent system, an optically determinable change characteristic for the component to be determined takes place. At least one signal formation reagent is present in the signal formation layer. In the evaluation region, there is provided a liquid transport layer which is an absorbent material which is in fluid contact with the liquid transport path. The signal formation layer runs parallel to the liquid transport layer, the signal formation layer is in liquid contact via a liquid exchange surface with the liquid transport layer perpendicularly to the plane of the base layer and the speed of liquid transport of the liquid transport layer and the chronological commencement of the signal formation reaction in the signal forming layer are adapted to one another in such a manner that the liquid first spreads out in the liquid transport layer and the signal formation reaction takes place substantially thereafter.

9 Claims, 1 Drawing Sheet

TEST CARRIER FOR THE ANALYTICAL DETERMINATION OF A COMPONENT OF A LIQUID SAMPLE

This application is a continuation of application Ser. No. 07/814,183, filed Dec. 19, 1991 now abandoned, which is a continuation of Ser. No. 07/384,982, filed Jul. 25, 1989, abandoned.

The present invention relates to a test carrier for the analytical determination of a component of a liquid sample and especially for the diagnosis of diseases by means of a reaction sequence taking place on the test carrier. The test carrier has several test layers. These comprise a base layer, a liquid transport path, which extends from a test application region into an evaluation region, and a signal formation region in which, on the basis of a signal formation reaction by means of a signal formation reagent system, there takes place an optically detectable change which is characteristic for the component to be determined.

For the qualitative or quantitative analytical determinations in the scope of the diagnosis of diseases, in recent times so-called carrier-bound tests have been used to an increasing extent. In these, reagents are embedded in appropriate layers of a solid test carrier which is brought into contact with the sample. The sample is usually a body fluid, for example blood or urine. However, it can also be a liquid obtained in a preceding test step, for example by contacting an elution agent with a faecal sample.

The reaction of the liquid sample with the reagents leads to a detectable signal, the present invention relating to cases in which an optically detectable signal is produced. It is usually a color change which takes place in the signal formation layer. Other optically detectable signal formation reactions lead, for example, to a fluorescence signal. The optically detectable change can be evaluated visually or by means of an appropriate apparatus, usually reflection photometrically.

Various signal formation reactions are used which can consist of several reaction steps in which several different reagents participate. These are, in all, referred to as a signal formation reagent system. A signal formation reagent of this system is usually to be found in the signal formation layer and participates in a reaction step which leads to the optically detectable change.

Test carriers are known in many different forms. The present invention is directed towards those test carriers which, as a rule, have a longitudinally extending base layer comprising a sample application region and an evaluation region. In such test carriers, the sample is applied to the sample application region and then transported along a liquid transport path which runs parallel to the base layer. Such "test carriers with longitudinal transport" have considerable advantages in comparison with the well-known test carriers with test layers exclusively arranged on top of one another and are especially well suited for immunological analysis processes. The liquid transport is based upon a capillary action in which the liquid transport path can be formed not only by one or more test layers of absorbent material, for example paper or fleece, but also by a gap which fills with liquid by capillary action. Test carriers with longitudinal transport are described, for example, in published Federal Republic of Germany Patent Applications DE-A 34 45 816, DE-A 36 43 516 and U.S. Pat. No. 4,839,297.

In published Federal Republic of Germany Patent Application DE-A 34 45 816, the signal formation layer, which is there referred to as the detection zone, is arranged beside other layers which form the liquid transport path. The sample liquid thereby flows through the signal formation layer in its longitudinal direction. Chromatography effects are thereby obtained which, in many cases of use, lead to a non-uniform color formation.

In the case of the test carrier described in U.S. Pat. No. 4,839,297, the signal formation layer is applied to a flap provided in the detection region which flap, in the initial stage of the test carrier, is not in fluid contact with the liquid transport path but rather is only pressed by an external mechanical manipulation (manually or with the help of an apparatus) downwardly against a liquid transport layer which is a part of the liquid transport path and, in this stage of use, is impregnated with the sample liquid. These measures make possible well defined color formation at a definite point of time but, nevertheless, require the mentioned mechanical manipulation.

In the case of the test carrier described in published Federal Republic of Germany Patent Application DE-A 36 43 516, a liquid transport path is provided which runs from a sample application zone to an absorption zone. On this liquid transport path, which is preferably formed by a gap, a signal formation layer is arranged in such a manner that it is in contact with a liquid flowing along the liquid transport path. A definite color formation is thereby aimed for in that the flow procedure in the liquid transport path and the absorbency properties of the signal formation layer are adapted to one another in a particular manner. There is achieved a readily reproducible dosing of the liquid taken up by the signal formation layer but the construction there described requires a laborious production.

It is an object of the present invention to achieve, in a test carrier with longitudinal transport, well defined conditions for the color formation reaction and a uniform color formation with low expense.

In accordance with the invention, a test carrier for the analytical determination of a component of a sample liquid, especially for the diagnosis of diseases, by means of a reaction sequence taking place on the test carrier, the test carrier comprises a) a base layer, b) a sample application region and an evaluation region, c) a liquid transport path, which extends from the sample application region to the evaluation region. The test carrier also includes d) a liquid transport layer in the liquid transport path and comprising an absorbent material and being in fluid contact with the liquid transport path. The test carrier also includes e) a signal formation layer containing at least one signal formation reagent of a signal formation reagent system and in which an optically detectable change characteristic for the component to be determined occurs by means of a signal formation reaction involving the signal formation reaction system, f) wherein the signal formation layer and the liquid transport layer are arranged parallel to each other such as to allow a liquid exchange in a direction perpendicular to the plane of the base layer via a liquid exchange surface, and g) wherein the speed of liquid transport in the liquid transport layer and the starting time of the signal formation reaction in the signal formation layer are adapted to one another in such a manner that the liquid first spreads out in the liquid transport layer and the signal formation reaction takes place substantially thereafter.

The term "fluid contact" is one which has become usual in test carrier technology for the case in which two test layers are so arranged with regard to one another that a liquid exchange between them is possible, mostly on the basis of the absorbency action of the test layers. The test layers can thereby be in direct contact with one another or the liquid contact can be brought about indirectly, for example by absorbent layers lying therebetween.

By means of the chronological adaptation according to the present invention, in the case of a test carrier with longitudinal transport, it is achieved that a homogeneously composed liquid front penetrates from the transport layer into the signal formation layer at a definite point of time. In this way, there is achieved a homogeneous and chronologically defined color formation. Extremely thin signal formation layers with a high concentration of signal formation reagent can be used without this leading to inhomogeneities of the color formation.

The signal formation layer and the liquid transport layer can be securely connected with one another insofar as the nature of the fixing does not hinder the liquid contact in the region of the liquid exchange surface. Both layers preferably lie loosely on one another in the region of the liquid exchange surface and are pressed together by appropriate means, for example a holding-down layer of synthetic material.

The liquid transport layer consists of an absorbent material, for example a paper, a textile structure (fabric or fleece) or, especially preferably, of a synthetic material membrane. Every kind of material has gaps or pores in which the liquid is transported by capillary forces. As is known, the speed of the liquid transport is influenced by the capillary forces prevailing in the layer and by the flow resistance of the layer. Further details in this regard are known to the expert and can be taken from appropriate publications, for example published Federal Republic of Germany Patent Application DE-A 36 43 516. However, because of the practical conditions in the case of the construction of test carriers, in many cases it is not possible to choose a liquid transport layer which fills up very quickly. On the contrary, in practice materials are frequently used in which the liquid is transported relatively slowly in the longitudinal direction of the layer. The signal formation reaction must then be correspondingly delayed in order to maintain the condition that it commences essentially after filling of the liquid transport layer.

This can, for example, be achieved by a signal formation reagent system containing an additional reagent which causes a pre-reaction which does not lead to a signal formation. In practice, in the case of analytical reactions of clinical chemistry, there is very frequently used an enzyme-catalyzed conversion of a color-forming substrate of an enzyme participating in the reaction as signal formation reaction. In this case, a delay of the color formation can be achieved in that, in addition to the color-forming substrate, there is used a non-color-forming substrate which has a higher affinity to the enzyme so that first the non-color-forming substrate reacts preponderantly and the color change first commences when the color-forming substrate has been substantially used up. This measure is explained in more detail in published Federal Republic of Germany Patent Application DE-A 36 40 318 for another purpose of use.

However, the signal formation is especially preferably delayed in that the solubility of the signal formation reagent in the signal formation layer is delayed. The signal formation reagent itself can be slowly soluble. However, the delayed dissolving behavior is preferably brought about in that the signal formation reagent is embedded in a less readily soluble film layer which is present on a base layer made from a foil or fabric. According to a further especially preferred embodiment, the signal formation reagent is more quickly soluble than the film layer in which it is embedded. It is thereby achieved that the signal formation reagent, when it is liberated from the signal formation layer, reacts quickly and homogeneously in the liquid phase. It is advantageous when the signal formation reagent then penetrates at least partly into the liquid transport layer so that the signal formation reaction takes place in part or, especially preferably, even preponderantly in the liquid transport layer.

It can be seen that in the case of all of the described processes for delaying the signal formation reaction, this already takes place to a small extent while the liquid is still spreading out in the liquid transport layer. It suffices, if the color formation reaction takes place in the sense of "essentially after the spreading out of the liquid", when an enrichment of colored materials in the liquid front, which flows in the liquid transport layer in the longitudinal direction of the test carrier, is avoided and a homogeneous signal formation is thereby achieved on the whole of the signal formation layer.

In order to bring about the desired delayed dissolving behavior, the signal formation layer preferably contains swellable macromolecules or a hydrophobic film former.

Swellable macromolecules in this sense are also called hydrocolloids. These are macromolecular hydrophilic substances which are soluble in water or are at least dispersable or swellable. These include, in particular, polysaccharides, for example exudates (such as gum arabic), seed meals (such as carob bean meal and starch), extracts from plants (such as pectins and alginates), microbial polysaccharides (such as xanthan gum) and chemically-modified polysaccharides (such as cellulose derivatives).

Certain proteins also belong to this group of substances, for example scleroproteins and hydrolysates thereof (for example collagen and crotein C), sparingly soluble reserve proteins (for example zein and precipitated casein) and hydrophobic dried proteins in correspondingly high concentrations (for example, serum albumin).

As hydrophobic film formers in the meaning of the present invention are to be understood water-soluble polymers which, in the case of drying, form from an aqueous solution a less readily soluble film in which, due to the adhesive action of the polymer, the materials contained in the film are fixed and bound.

The dissolving properties of such films can be controlled to a large extent by choice of the polymers. These include, for example, polyvinyl alcohols such as are commercially available under the trademark "MOWIOL" from Hoechst A. G. Frankfurt, Federal Republic of Germany (FRG), polyethylene oxide, such as is commercially available under the trademark "POLYOX" from the Union Carbide Corporation, New York, U.S.A., and acrylic resins such as are obtainable from the firm Roehm, Darmstadt, FRG, under the trademark "EUDRAGID".

For a better understanding of the invention, together with other and further objects thereof, reference is made to the following description, taken in connection with the accompanying drawings, and its scope will be pointed out in the appended claims.

Figure 2:
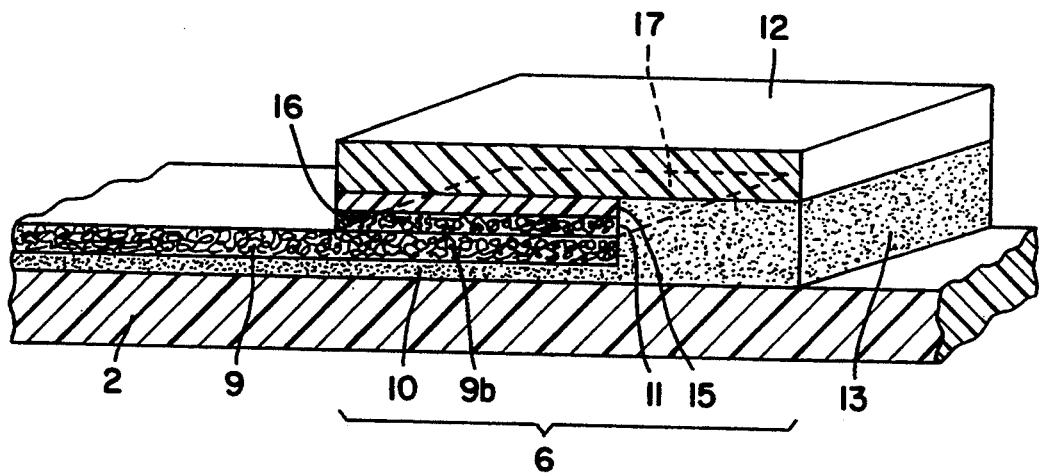

The present invention is especially suitable for a test carrier for carrying out immunological determinations as is described in more detail in the following with reference to an embodiment illustrated schematically in the accompanying drawings, in which FIG. 1 is a perspective view of a test carrier according to the present invention; and FIG. 2 shows an enlarged view of a portion of the test carrier of FIG. 1.

The test carrier 1 illustrated in the Figures has a base layer 2 on which are affixed the other test layers. In its longitudinal direction, the test carrier can be divided up into a sample application and pre-reaction region 4 and into an evaluation region 6. In the sample application and pre-reaction region 4, a conjugate layer 8 and a liquid transport layer 9 are fixed next to one another on the base layer 2 with the help of a melt adhesive 10. The layer 8 slightly overlaps the subsequent layer 9 in order to ensure liquid contact between them which is as good as possible. The layers 8 and 9 consist of absorbent material and form a liquid transport path which extends from the sample application and pre-reaction region 4 into the evaluation region 6.

In the illustrated example, the sample is applied to the conjugate layer 8, this layer simultaneously serving for carrying out a first reaction step. Therefore, the region 4 represents a combined sample application and pre-reaction region. Alternatively, in FIG. 1 to the left of the conjugate layer 8 there can also be provided a special sample application layer which defines a sample application region separate from the pre-reaction region.

In the evaluation region 6 are to be seen on the base layer 2, as can be seen more clearly from FIG. 2, over one another the liquid transport layer 9, a signal formation layer 11 and a holding-down layer 12. The holding-down layer 12 consists of a comparatively stiff synthetic material film. It is so fixed, with the help of a melt adhesive strip 13 of corresponding larger layer thickness, to the base layer 2 that it runs parallel to it at a distance which corresponds to about the total thickness of the signal formation layer 11 and liquid transport layer 9. The holding-down layer 12 has a stiffness which is sufficient so to press together the layers present between it and the base layer 2 that a good fluid contact is ensured between them.

Advantageously, besides the color formation layer, on its side facing away in the longitudinal direction of the base layer 2 from the sample application region (thus, in FIG. 1 on the right of the signal formation layer 11), no further absorbent layers are provided. Thus, the signal formation layer 11 is in liquid contact with the last section of the liquid transport.

In the illustrated preferred embodiment, the signal formation layer 11 consists of a layer 15 and a film layer 16 of delayed solubility present thereon which contains a signal formation reagent.

The test carrier illustrated in the FIGURES is, as mentioned, especially suitable for immunological determinations. Such determinations utilize highly specific binding reactions between various species which can be referred to as binding partners. Immunological binding partners are especially antibodies, on the one hand, as well as antigens or haptens, on the other hand.

For the case in which an antigen AG contained in the sample is to be determined as analyte, the following course of reaction is typical.

The conjugate layer is so named because it contains a soluble conjugate of antibody "AB" and enzyme "E", and the conjugate is referred to as "ABE". The antibody portion of the conjugate is specifically bindable with antigen "AG". Complexes of AG-ABE result due to the specific binding reaction.

Excess ABE, together with the AG-ABE complexes, passes into the liquid transport layer 9. This contains an antigen AGF in carrier-fixed form. The AGF is identical with the sample antigen or analogous to this, i.e. specifically bindable with the antibody of the ABE contained in the conjugate layer 8.

On the basis of the specific binding reaction, the excess free conjugate is now carrier-fixed with the fixed antigen in the layer 9. To this end it is important that the coating density of the fixed antigen on the layer 9 and especially in the part 9a of this layer which is located in the pre-reaction zone 4 is high enough to ensure that practically the whole excess conjugate is bound thereon. The part 9a of the layer 9 is, therefore, referred to as "fixing layer". Only the free AG-ABE complexes pass into the part 9b of the layer 9 which is located in the evaluation zone 6. The amount of the AG-ABE complexes (and thus the amount of the labelling enzyme) thereby corresponds to the amount of the analyte.

On the basis of the present invention, the part 9b of the liquid transport layer 9 is completely filled essentially before the signal formation reaction with the signal forming reagent in the layer 11 commences. Only when the liquid has fully spread out in the layer 9b does the signal formation reaction commence, whereby, as described above, this is preferably achieved in that the signal formation layer 11 dissolved retardedly.

According to the present invention, the liquid in the layer 9b initially spreads out "laterally", i.e. in the direction parallel to the surfaces of the layer (and thus in the longitudinal direction of the test carrier). The color formation in the layer 11 essentially only commences thereafter. The liquid penetrates from the part 9b of the layer 9 vertically to the surface thereof through the liquid exchange surface 17 illustrated by broken lines in FIG. 2 uniformly into the signal formation layer, dissolves (in the described example) a color-forming substrate for the labelling enzyme of the conjugate contained therein and catalyses its color-forming reaction. The color change is thus a measure for the concentration of the enzyme and thus for the concentration of the analyte.

In the illustrated case, the fixing layer 9a is a part of the liquid transport layer 9. A separate layer could also be used as fixing layer which is in fluid contact with the liquid transport layer. However, the use of a single layer, which extends partly as fixing layer into the pre-reaction region and which partly in the detection region provides the transport parallel to the signal formation layer, is preferred because it permits a simple construction and reduces the need for sample liquid. In this case, the layer material must be so chosen that it permits a high coating density with the fixed antigen and the speed of transport is relatively slow in order to make possible the fixing of the excess conjugate. It is here especially important that the signal formation reagent in the signal formation layer is less soluble.

The manner of operation of the test carrier has been described, by way of example, for the case in which an antigen is to be determined. An analogous course of the test is also possible for the determination of an antibody in which case an antigen conjugate has to be used in the layer 8 and a carrier-fixed analogous antibody in the layer 9.

In general, the test carrier according to the present invention is especially suitable for those determinations in which the reaction sequence includes a specific binding reaction between a first binding partner correlated with the concentration of the component to be determined (in the case of the example AG) and a labelled second binding partner (in the case of the example ABE) with the formation of mobile complexes (in the case of the example AG-ABE) and a further specific binding reaction between the second binding partner (in the case of the example again ABE) and a carrier-fixed third binding partner (in the case of the example AGF) analogous to the first binding partner. It is thereby necessary that the second and third binding partner, in each case referred to the direction of flow of the liquid, are arranged in the test carrier before the detection region thereof, thus in a pre-reaction region lying outside of the detection region. The specific binding reaction is thereby concluded before the free complexes specific for the analysis pass into the detection region.

Apart from the peculiarities of the present invention, the described immunological course of the test is similar to that described in U.S. Pat. No. 4,839,297.

The test carrier according to the present invention is especially suitable as a detection unit for a test kit for the determination of an analyte in feces, such as is described in published Federal Republic of Germany Patent Application DE-A 37 16 891. This test kit has a sample collection unit in which a liquid is obtained from the fecal samples by means of elution with the help of an elution agent, this liquid containing the analyte. The sample liquid thus obtained can be advantageously investigated with the test carrier according to the present invention.

The following Examples are given for the purpose of illustrating the present invention. Example 1 is concerned with a test carrier in which, as analyte, there is determined human serum albumin (hSA) which has been eluted from a fecal sample and is an indicator for the presence of blood in feces.

EXAMPLE 1

A test carrier according to FIGS. 1 and 2 of the accompanying drawings is produced as follows:

a) Conjugate layer 8:

IgG <human serum albumin> is covalently conjugated with β-galactosidase. This conjugate is impregnated into a glass fiber fleece and dried. The test layer size on the test carrier is 20×6 mm.

b) Liquid transport layer 9 (also the fixing layer):

hSA is covalently fixed on a membrane of hydrophilic polyvinylidene difluoride (PVDF) of the firm Millipore (Bedford, U.S.A.) which is commercially available under the trademark IMMOBILON AV. The surface concentration is adjusted via the concentration in the buffer used for the impregnation procedure to 20 μg. hSA/cm$^2$. The size of the layer is 20×6 mm.

c) Signal formation layer 11:

A film-forming coating mass is produced using 0.6% Ketrol F of the firm Kelco, Hamburg, Federal Republic of Germany (FRG) with the addition of 2.5% methylcellulose 15 of the firm Serva, Heidelberg, FRG. It contains 12 mM chlorophenol red-β-galactoside (CPRG) and is buffered in HEPES. The coating mass is coated in a film layer thickness of 200 μm. on to a 100 μm thick carrier film of Pokalon of the firm Lonza, Weil/Rh., FRG. The size of the layer is 6×6 mm.

d) Holding-down layer 12:

This consists of a 140 μm. thick Pokalon film.

As base layer, there is used a polyester film "MELINEX" of the firm I. C. I., Frankfurt, FRG. The adhesion of the components takes place with melt adhesive Dynapol S 1358 of the firm Dynamid Nobel, Troisdorf, FRG.

The liquid front moves comparatively slowly in the layer 9 so that the spreading out of liquid in the layer requires almost three minutes. Nevertheless, due to the slow dissolving behavior of the substrate layer 11, completely homogeneous color formation is achieved in dependence upon the hSA concentration which permits a determination of this concentration with good exactitude.

In the following Examples 2 to 4, there are compared different formulations for a signal formation layer 11 and of its film layer 16, respectively, and the dissolving behavior thereof compared.

EXAMPLE 2

To a base formulation for a color forming film (substrate film) consisting of

| | |
|---|---|
| 30 g. | Keltrol F, a xanthan of the firm Kelco, Brussels, Belgium (1% in 50 mM, HEPES, pH 7.0) |
| 17 g. | CPRG (30 mM in water) |
| 3. g. | 200 mg. Tween 20 (firm Serva, Heidelberg, FRG) + 50 mg. magnesium chloride in 2.75 g. water | are added different substances in order to compare the behavior thereof with regard to a delay of the solubility of the inherently readily soluble xanthan film layer (see U.S. Pat. No. 4,876,067). The time is compared within which such a film, after wetting with water, has dissolved to such an extent that it can be completely wiped off. The following results are thereby obtained:

| | dissolving retardant | can be wiped off after |
|---|---|---|
| a) | base formulation | immediately |
| b) | 2% methylcellulose 15 (water-soluble cellulose ether M.W. 14,000, Serva, Heidelberg, FRG) | 5 seconds |
| c) | 2% Ficoll 70 (co-polymer of sucrose and epichlorohydrin, Serva) | 2 seconds |
| d) | 2% Crotein C (collagen hydrolysate, firm Croda, Cheshire, England) | 2 seconds |
| e) | 2% Mowiol 18/88 (partially saponified polyvinyl alcohol of the firm Hoechst, Frankfurt, FRG) | 2 seconds |

The delaying of the solubility appears to be short in comparison with the slow spreading out of the liquid in the liquid transport layer 9 mentioned in Example 1. However, it must be borne in mind that the wiping off is a mechanical stressing of the layer which does not occur in the test carrier. Therefore, the dissolving delay achieved here is sufficient in practice. The wiping off test permits the choice of suitable film formulations.

EXAMPLE 3

Influence of different amounts of methylcellulose 15

To the base formulation of Example 2 are added different amount of methylcellulose 15 and the wiping off times are observed. The following results are obtained:

|     | concentration of methylcellulose 15 | can be wiped off after |
|-----|-------------------------------------|------------------------|
| (0) | 0                                   | immediately            |
| (1) | 0.1%                                | immediately            |
| (2) | 0.5%                                | 1 second               |
| (3) | 1.0%                                | 2 seconds              |
| (4) | 2.0%                                | 5 seconds              |
| (5) | 5.0%                                | 15 seconds             |

EXAMPLE 4

Another film for a signal formation layer 11 with a dissolving off period of 10 seconds can be produced with the following formulation with the use of a hydrophobic film former:

30.0 g. Mowiol 8/88 (23% in 20 mM HEPES, pH 7.2)
16.7 g. CPRG solution (30 mM in 20 mM HEPES, pH 7.2)
0.2 g. Tween 20
0.1 g. magnesium chloride
3.0 g. water While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. Test carrier useful in determination of a component of a liquid sample, comprising:
   (A) a base layer,
   (B) a liquid transport path comprising, in longitudinal array:
      (i) a sample application region,
      (ii) a preevaluation region and
      (iii) an evaluation region, and;
   (C) a signal formation layer, wherein:
      (a) said liquid transport path is parallel to said base layer,
      (b) said liquid transport path contains a plurality of binding partners, at least one of which is labelled, wherein said plurality of binding partners are positioned in said liquid transport path prior to said evaluation region, so that said labeled binding partner forms a mobile, labeled complex in the presence of said component which is indicative thereof,
      (c) said evaluation region comprises an absorbent, liquid transport layer which, prior to application of said liquid sample is in fluid communication with said sample application region and said preevaluation region thereby permitting liquid exchange,
      (d) said signal formation layer contains a soluble signal forming reagent, which when contacted with said liquid sample is liberated from said signal formation layer and reacts with said mobile labeled complex to form an optically detectable signal indicative of said component in the liquid phase,
      (e) said liquid transport layer of said evaluation region and said signal formation layer are positioned parallel to each other, and prior to application of said liquid sample are in fluid communication, permitting liquid exchange in a direction perpendicular to said base layer, said parallel arrangement of said signal formation layer to said liquid transport layer for fluid communication being at the last section of said liquid transport path, and
      (f) said soluble signal forming reagent is embedded in a slowly soluble film layer, said signal formation reagent being more rapidly soluble than said slowly soluble film layer and liquid moves in said liquid transport layer at a speed which permits spreading out therein in a direction parallel to said base layer prior to dissolving said slowly soluble film and formation of said optically detectable signal,
   whereby said liquid sample first spreads laterally in said liquid transport path in a direction parallel to said liquid transport layer surface and then uniformly penetrates the signal formation layer in a direction perpendicular to the base layer from the liquid transport layer, and dissolves said slowly soluble film layer and said color forming reagent contained therein, so as to allow said signal forming reagent of subpart (d) to react in the liquid phase with said mobile, labelled complex of subpart (b).

2. Test carrier according to claim 1, wherein the signal formation layer and the liquid transport layer lie loosely upon one another in the region of the liquid exchange surface.

3. Test carrier according to claim 1, wherein the signal formation layer contains a water-swellable macromolecular substance.

4. Test carrier according to claim 1, wherein the signal formation layer contains a hydrophobic film forming material.

5. Test carrier according to claim 1, wherein the signal formation reagent in the signal formation layer is a color-forming substrate for an enzyme participating in the analysis reaction.

6. Test carrier according to claim 5, wherein the substrate is chlorophenol red-$\beta$-galactoside.

7. Test carrier according to claim 1, wherein said parallel arrangement of layers at the last section of said transport path is covered by a holding-down layer consisting of a stiff synthetic material film which is fixed by a melt adhesive strip to the base layer so that said holding-down layer runs parallel to said base layer at a distance which corresponds to the total thickness of said parallel arrangement, the stiffness of the holding-down layer being sufficient to press together the layers of the parallel arrangement so that good fluid contact between them is achieved.

8. Test carrier of claim 1, wherein said plurality of binding partners comprise (i) a first binding partner, (ii) a second, labeled binding partner which specifically binds said first binding partner and (iii) a third, carrier fixed binding partner which is analogous to said component.

9. Test carrier of claim 8, wherein said third, carrier fixed binding partner is positioned in said preevaluation region.

* * * * *